(12) United States Patent
Cunningham (10) Patent No.: US 8,715,240 B2
(45) Date of Patent: May 6, 2014

(54) APPARATUS AND METHOD FOR CONVECTION ENHANCED THERAPEUTIC DELIVERY

(75) Inventor: Miles G. Cunningham, Charlestown, MA (US)

(73) Assignee: The McLean Hospital Corporation, Belmont, MA (US)

( * ) Notice: Subject to any disclaimer, the term of this patent is extended or adjusted under 35 U.S.C. 154(b) by 1145 days.

(21) Appl. No.: 12/123,031

(22) Filed: May 19, 2008

(65) Prior Publication Data

US 2008/0287917 A1  Nov. 20, 2008

Related U.S. Application Data

(60) Provisional application No. 60/938,784, filed on May 18, 2007.

(51) Int. Cl.
*A61M 5/178* (2006.01)
*A61M 25/00* (2006.01)
*A61B 17/24* (2006.01)

(52) U.S. Cl.
USPC ............... 604/164.01; 604/264; 604/170.02; 604/170.01; 606/113

(58) Field of Classification Search
USPC ........ 604/510, 95.01, 22, 158, 264, 523, 528, 604/921, 164.01, 171, 263, 170.01, 170.02; 33/510, 95.01, 22, 158, 264, 523, 528, 33/921; 606/113, 114, 127, 110
See application file for complete search history.

(56) References Cited

U.S. PATENT DOCUMENTS

| | | | |
|---|---|---|---|
| 5,267,958 A | | 12/1993 | Buchbinder et al. |
| 5,281,236 A | * | 1/1994 | Bagnato et al. ............... 606/139 |
| 5,318,527 A | * | 6/1994 | Hyde et al. ................. 604/95.04 |
| 5,545,135 A | * | 8/1996 | Iacob et al. ................. 604/103.1 |
| 5,573,008 A | * | 11/1996 | Robinson et al. ............. 600/567 |
| 5,792,110 A | | 8/1998 | Cunningham |
| 6,251,092 B1 | * | 6/2001 | Qin et al. .................... 604/95.01 |
| 6,517,550 B1 | * | 2/2003 | Konya et al. .................. 606/113 |
| 6,682,501 B1 | * | 1/2004 | Nelson et al. .................... 604/22 |
| 6,740,104 B1 | | 5/2004 | Solar et al. |
| 7,108,696 B2 | * | 9/2006 | Daniel et al. ..................... 606/41 |
| 2003/0118563 A1 | * | 6/2003 | Loeb .......................... 424/93.21 |

FOREIGN PATENT DOCUMENTS

| | | |
|---|---|---|
| EP | 1428546 A2 | 6/2004 |
| WO | WO89/09079 | 5/1989 |
| WO | WO92/12755 | 8/1992 |

\* cited by examiner

*Primary Examiner* — Bhisma Mehta
*Assistant Examiner* — Bradley G Thomas, Jr.
(74) *Attorney, Agent, or Firm* — Preti Flaherty Beliveau & Pachios LLP (57) ABSTRACT

A system for convection enhanced delivery of therapeutic comprises one or more flexible, biocompatible microcatheters that are directed to a target location to deliver a therapeutic agent. The microcatheter is releasably coupled to a guide tube and directed to the desired location. The microcatheters are small and flexible in order to reach the target areas, minimize trauma at the injection site, and minimize reflux of the injectable therapeutic.

23 Claims, 5 Drawing Sheets

APPARATUS AND METHOD FOR CONVECTION ENHANCED THERAPEUTIC DELIVERY

RELATED APPLICATIONS

This application is a non-provisional application claiming priority from U.S. provisional application Ser. No. 60/938,784, filed May 18, 2007, entitled "Convection Enhanced Delivery System," the entire contents of which is hereby incorporated by reference for all purposes.

FIELD OF THE INVENTION

The present invention is related to convection enhanced delivery of a therapeutic for treatment of tumors, more specifically, treating tumors in the brain.

BACKGROUND

Malignancies of the brain are among the most devastating diseases known. In the US, the prevalence of brain cancer is 360,000, with 15,000 deaths per year. A large percentage of these malignancies are found to be glioblastoma multiforme (GBM), having a very rapid, aggressive, and uncontrolled growth. Very little progress has been made in the treatment of GBM over the past 25 years. Present therapeutic approaches involve surgical excision, chemotherapy, and radiation therapy. The death rate of patients who have been diagnosed as having GBM, however, is 98%. Patients rarely survive for more than one year from diagnosis, often dying within six months. There is on-going research in how to effectively treat GBM.

One experimental approach is "targeted toxin therapy," in which chemotherapeutics are directly infused into the tumor and the surrounding tissue where the tumor cells begin to infiltrate. This method, while requiring a surgical procedure, has been shown to reduce the debilitating side effects seen with systemic administration. It also reduces concerns regarding medicine crossing the blood brain barrier (BBB), and may achieve very high concentrations of therapeutic agent directly within, and in the vicinity of, the tumor.

Numerous agents for targeted toxin therapy are currently in clinical development. One such targeted toxin is cintredekin besudotox (CB), which is a recombinant protein made up of interleukin-13 and an active toxic protein derived from Pseudomonas exotoxin TP-38. CB binds selectively to the IL-13-overexpressing malignant glioma cells. Other agents being evaluated include standard anti-mitotic chemotherapy agents, transferrin-conjugated toxins, and radioisotope conjugates.

A delivery method for these medicines currently being evaluated is known as "convection-enhanced delivery" (CED), in which the tumor and surrounding tissue are deluged with high volumes of therapeutic agent under positive pressure. This method was designed by NIH researchers to facilitate the infiltration into brain tissue of high molecular weight therapeutic molecules that would not ordinarily diffuse over appreciable distances if simply injected. The parameters for effective CED have been extensively studied and modeled.

Delivery devices to accomplish CED remain under development. Presently, large bore catheters are surgically placed within the malignant mass and an infusion pump is used to drive flow at a rate of approximately 3 mL per hour for extended periods, e.g., up to 4 days. Various catheters have been designed and tested, usually having outer diameters (OD) of 1 mm or greater. Human CED trials are being performed using ventricular shunt tubing (2.1 mm OD) or spinal drains, e.g., 18 gauge, or 1.2 mm in diameter, as delivery cannulas.

These CED delivery methods have a number of shortcomings associated with the size of the delivery catheters. Under high-flow conditions, backflow (or reflux) of the injectable therapeutic occurs in a proximal direction along the outer catheter walls, resulting in a loss of the therapeutic into spaces and regions where it is not intended, and a loss of the pressure required to enable convection of the therapeutic molecules within an interstitial space. These shortcomings are particularly problematic in situations where the tumor is more superficial, as the segment of catheter that is surrounded by brain tissue is reduced. For targets that are deep within the brain, the length of catheter that is surrounded by tissue is increased, and the resistance to back flow is, therefore, also increased. To mitigate this situation, surgery is planned so that the cannula trajectory traverses the longest possible track through the parenchyma to minimize reflux. It has been observed, however, that the larger diameter catheters do not permit precise placement, which is an issue as it is required for more targeted or discrete delivery. Moreover, inserting multiple larger catheters is cumbersome and may limit wide distribution of the therapeutic.

Smaller diameter catheters have been shown to decrease backflow because the amount of backflow decreases as a function of the catheter diameter to the power of four-fifths.

Smaller diameter catheters have less rigidity, therefore, they have required construction in a telescoping, or "step design," in order to obtain a final catheter diameter of approximately 0.168 mm. Known telescope designs use smaller diameter tubing glued to the end of a rigid stainless steel cannula. The rigid tube, however, is problematic for situations in which it must be left in place, e.g., in the brain, for extended periods of time measured in hours or days. The rigid portion presents a risk to the patient due to, for example, accidental contact and/or movement. Furthermore, while a final diameter of 0.168 mm minimizes reflux, the rate of delivery may be compromised.

SUMMARY

In one embodiment, an apparatus for delivering a therapeutic to a location in a body comprises: a hollow guide tube comprising a lumen therethrough with distal and proximal openings, the guide tube comprising an outer diameter in a range of 0.5 to 1.2 mm; a stylet, having proximal and distal portions, disposed within the guide tube lumen, wherein the stylet distal portion extends distally from the guide tube distal opening; a catheter having a catheter lumen running from a distal opening to a proximal opening, the catheter lumen having a diameter in a range of 0.03 to 2.11 mm; and a loop attached to a catheter distal portion, the loop releasably coupled to the stylet distal portion.

In another embodiment, a method of delivering a therapeutic to a target region in a body, the method comprises: providing a hollow guide tube comprising a lumen therethrough with distal and proximal openings, the guide tube having an outer diameter in a range of 0.5 mm to 1.2 mm; disposing a stylet, having proximal and distal portions, within the guide tube lumen, and extending the stylet distal portion distally from the guide tube distal opening; providing a catheter having a distal portion and releasably coupling the catheter distal portion to the stylet distal portion, the catheter comprising a catheter lumen having a diameter in a range of 0.03 mm to 2.11 mm and running from a distal opening to a proximal opening; distally inserting the releasably coupled guide tube, stylet and catheter into the body and locating the distal portion of the catheter in the target region; withdrawing the stylet proximally through the tube and releasing the catheter from the stylet; withdrawing the guide tube from the body and leaving the distal opening of the catheter in the target region; coupling the catheter to a source of the therapeutic; and delivering the therapeutic to the target region through the catheter.

In one embodiment, a method of delivering a therapeutic to a target region in a body comprises: providing a catheter having a catheter lumen having a diameter in a range of 0.03 mm to 2.11 mm and running from a distal opening to a proximal opening; disposing a stylet within the catheter lumen; distally inserting the coupled stylet and catheter into the body and locating the distal opening of the catheter in the target region; withdrawing the stylet proximally through the catheter and leaving the distal opening of the catheter in the target region; coupling the catheter to a source of the therapeutic; and delivering the therapeutic to the target region through the catheter.

In yet another embodiment, a kit for delivering a therapeutic by convection enhanced delivery to a location in a body comprises: a hollow guide tube comprising a lumen therethrough with distal and proximal openings, wherein the guide tube has an outer diameter in a range of 0.5 mm to 1.2 mm; a stylet, having proximal and distal portions, configured to be disposed within the guide tube lumen, wherein the stylet distal portion is configured to extend distally from the guide tube distal opening; a catheter having a catheter lumen running from a distal opening to a proximal opening, the catheter lumen having a diameter in a range of 0.03 mm to 2.11 mm; a loop coupled to a distal portion of the catheter and configured to be releasably coupled to the stylet distal portion; and instructions for using the hollow guide tube, stylet, and catheter to deliver a therapeutic by convection enhanced delivery by: disposing the stylet within the guide tube lumen, and extending the stylet distal portion distally from the guide tube distal opening; releasably coupling the loop on the catheter distal portion to the stylet distal portion; distally inserting the releasably coupled tube, stylet and catheter into the body and locating the distal portion of the catheter in a target region; withdrawing the stylet proximally through the tube and releasing the catheter from the stylet; withdrawing the guide tube from the body and leaving the catheter distal opening in the target region; coupling the catheter to a source of the therapeutic; and delivering the therapeutic to the target region through the catheter.

In yet another embodiment, a kit for delivering a therapeutic by convection enhanced delivery to a location in a body comprises: a catheter having a catheter lumen running from a distal opening to a proximal opening, the catheter lumen having a diameter in a range of 0.03 mm to 2.11 mm; a stylet, having proximal and distal portions, configured to be disposed within the catheter lumen; and instructions for using the stylet and catheter to deliver a therapeutic by convection enhanced delivery by: disposing the stylet within the catheter lumen; distally inserting the stylet and catheter into the body and locating the distal opening of the catheter in a target region; withdrawing the stylet proximally through the catheter lumen and leaving the catheter distal opening in the target region; coupling the catheter to a source of the therapeutic; and delivering the therapeutic to the target region through the catheter.

BRIEF DESCRIPTION OF THE DRAWINGS

Embodiments of the present invention may be better understood by referring to the following description in conjunction with the accompanying drawings in which.

DETAILED DESCRIPTION

The various embodiments of the invention are herein described with reference to the accompanying drawings. It is stressed that the particulars shown are by way of example and for purposes of illustrative discussion of the various embodiments of the present invention only. These are presented in the cause of providing, what is believed to be, the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms and embodiments of the present invention may be embodied in practice.

Prior to explaining at least one embodiment of the present invention in detail, it is to be understood that the present invention is not limited in its application to the details of construction and the arrangement of the components set forth in the following description or as illustrated in the drawings. The invention is capable of other embodiments or of being practiced or carried out in various ways. Also, it is to be understood that the phraseology and terminology employed herein are for the purpose of description and should not be regarded as limiting.

It is advantageous to be able to direct a small diameter catheter to a specific location, e.g., a tumor in a brain, to deliver a therapeutic as the smaller diameter minimizes backflow and, therefore, more therapeutic is delivered where needed. Small diameter catheters, however, do not have sufficient rigidity to allow for repeatable and accurate placement. As will be described in more detail below, in various embodiments of the present invention, a convection enhanced delivery system ("CEDSYS") and corresponding method employs an array of microcatheters or micro-cannula that can be stereotactically placed in order to distribute a therapeutic to, for example, uniform or irregularly-shaped intracerebral targets.

The term "therapeutic" is defined herein as any substance that is deliverable using the methods described below. These substances are typically, but not limited to, medicines in a fluid medium used to treat disease, to restore or improve function of central nervous system (CNS) regions, i.e., tissues comprised by the brain and spinal cord, or to destroy or impair dysfunctional or rogue tissue or other material within the CNS. In addition, a therapeutic may comprise a capsule or micro-capsule, powder, gel, solid, or gas.

Figure 1:
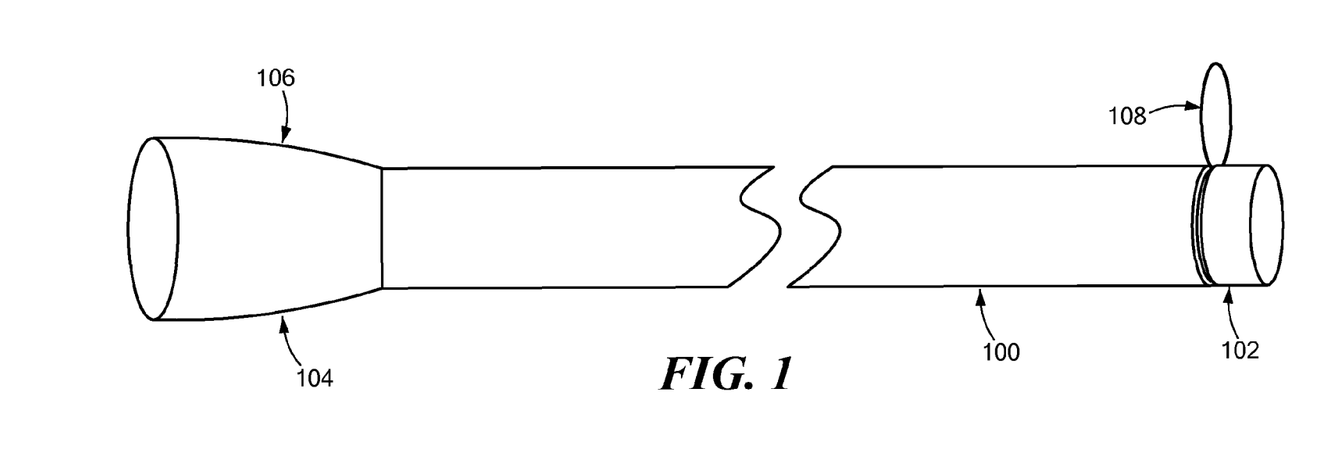
FIG. 1 represents a microcatheter according to one embodiment of the present invention.

Referring now to FIG. 1, in accordance with an embodiment of the present invention, a microcatheter 100 is composed of bio-compatible tubing, e.g., polyimide, with an internal diameter (ID) range of about 0.03 mm to 2.11 mm, and an outer diameter (OD) ranging from about 0.05 mm to 3 mm. As known to those of ordinary skill in the art, a length of the microcatheter 100 is sufficient to allow for connection to any equipment needed for the procedure. The microcatheter 100 may also be referred to as a micro-cannula, however, the terms as used herein are interchangeable and not meant to be limiting.

A distal portion 102 of the microcatheter 100 may be impregnated with an MRI detectable or otherwise radio-opaque material to facilitate viewing and evaluation of placement. This material may be confined to the distal portion 102 of the tubing. In an alternate embodiment, the entire microcatheter 100 may be radio-opaque or MRI detectable. A proximal end 104 of the microcatheter 100 is attached to a universal adaptor 106, e.g., a Luer fitting. A loop or ring 108 is affixed to the distal exterior portion 102 of the microcatheter 100.

Figure 2A:
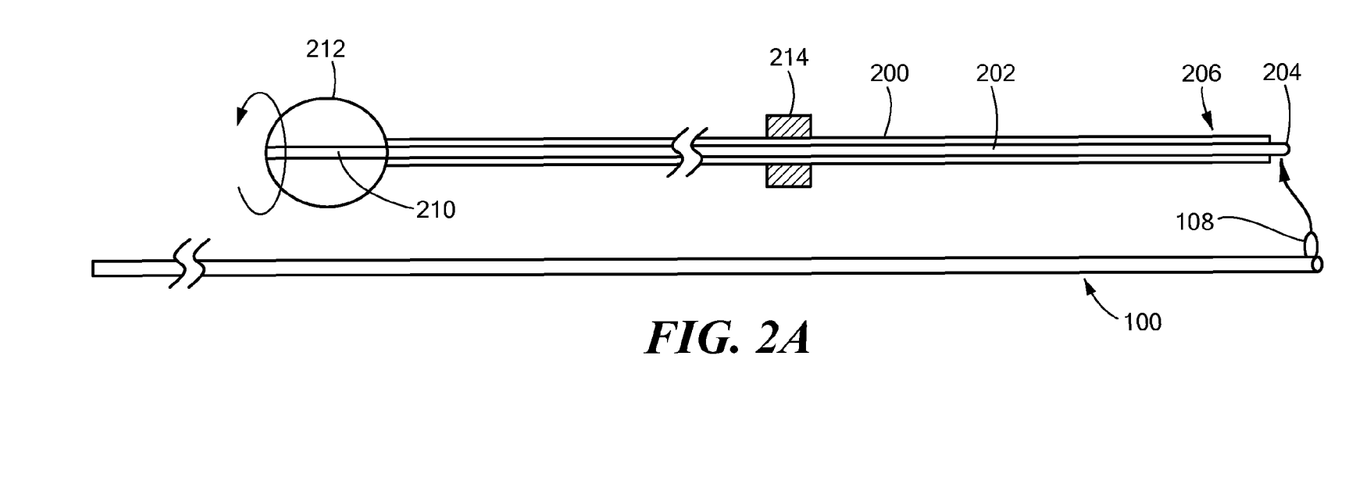
FIGS. 2A and 2B represent an inserter and the microcatheter of FIG. 1 arranged in accordance with an embodiment of the present invention.

Referring now to FIG. 2A, a small-gauge stereotactic inserter or guide tube 200, e.g., an inserter similar to one produced by Preferred Instruments, Inc. is provided. The inserter 200 is composed of stainless steel hollow tubing with a diameter of 0.5-1.2 mm. A solid stylet 202 with a rounded distal portion 204 is placed within the guide tube 200 and extends beyond a distal portion 206 of the guide tube 200 by approximately 0.5 to 1 mm. The solid stylet 202 may be a metal such as: stainless steel, platinum, cobalt, titanium, or tantalum, or similar metal, any of which could be in either an alloy or pure form. The stylet 202 may have a diameter in the range of 0.1 to 2.0 mm. In an alternate embodiment, the stylet is not solid but sufficiently stiff or resistant to bending so as to facilitate insertion as explained below.

Figure 2B:
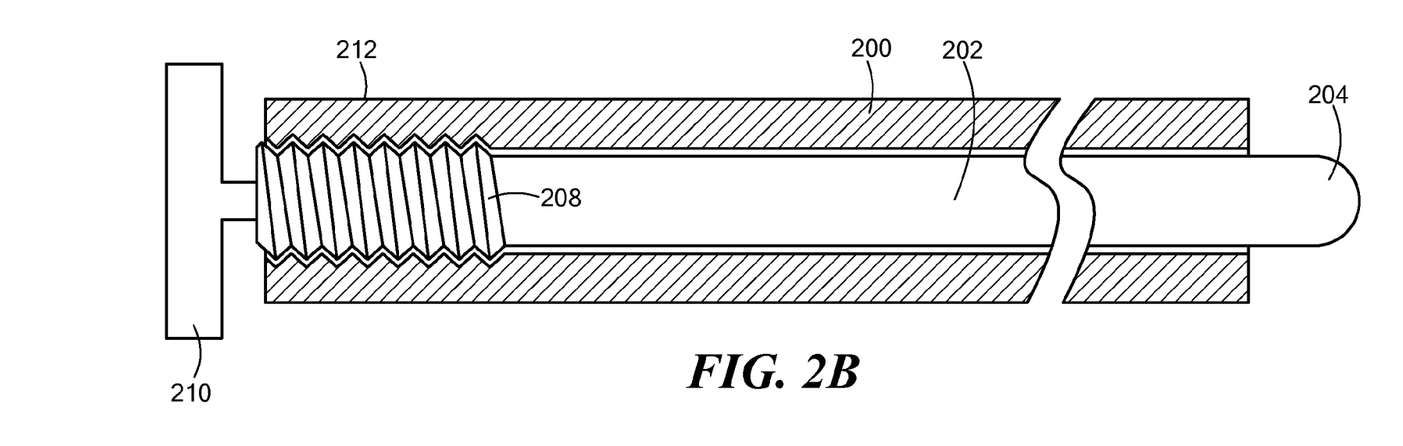

As shown in FIG. 2B, an enlarged cross-sectional view of that shown in FIG. 2A, a proximal end 208 of the stylet 202 is fixed permanently to a thumbscrew 210 that treads within a threaded portion 212 of the guide tube 200. Thus, upon turning the thumbscrew 210 the stylet 202 is moved within the guide tube 200.

The inserter 200 may also incorporate a stop 214 that may be moved along the length of the guide tube 200 and locked at any location along the length. The stop 214 may comprise a set screw or the like. The stop 214 provides an indicator to allow for precise depth placement of the guide tube 200 during a stereotactic procedure.

Figure 5:
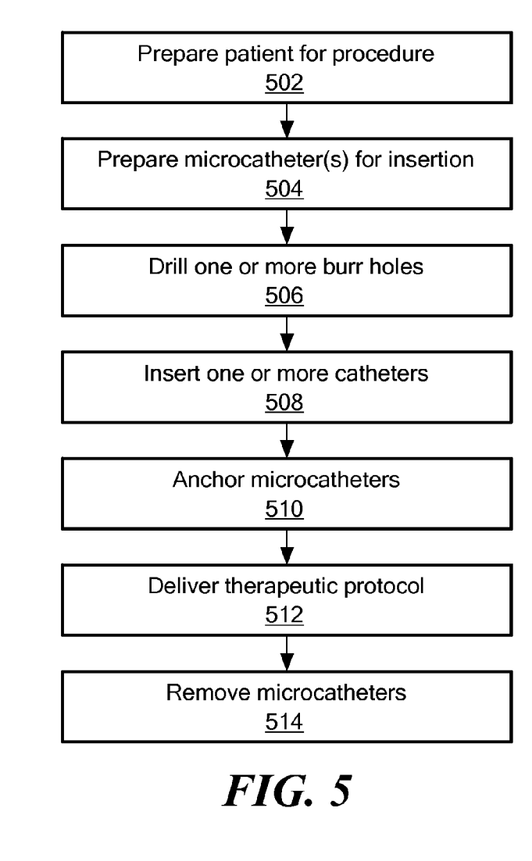
FIG. 5 is a method of inserting a microcatheter in accordance with one embodiment of the present invention.

In accordance with one embodiment of the present invention, a method 500, referring to FIG. 5, for inserting one or more microcatheters 100 in, for example, the brain of a patient, will be described.

Initially, step 502, neuroimaging is performed and the patient is prepared for stereotactic surgery as known to those of ordinary skill in the art. The preparation may include determining sites in the brain 300 for microcatheter 100 placement with respect to an affected area 306.

Figure 3:
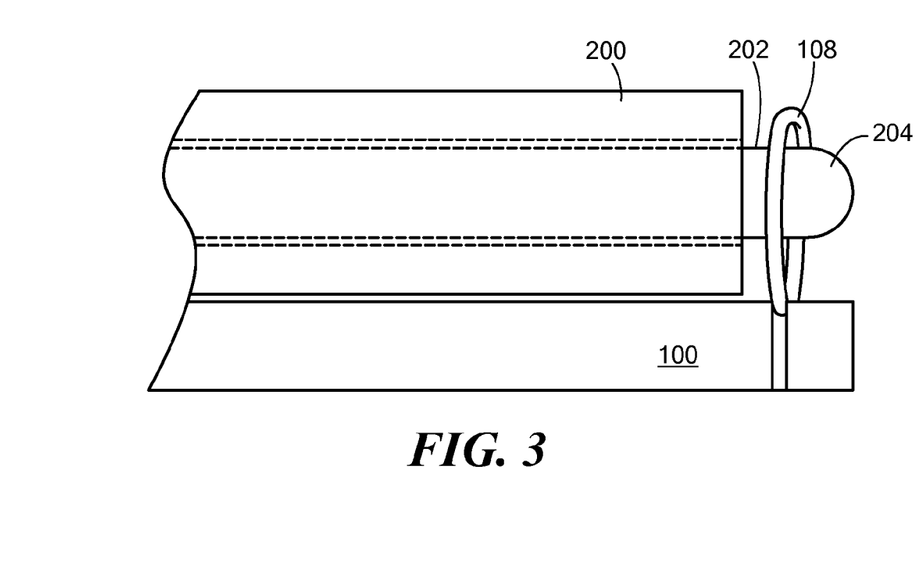
FIG. 3 is a close-up view of a distal portion of the system shown in FIGS. 2A and 2B.

Subsequently, or at the same time as the preparation above, the microcatheters 100 are releasably coupled to the inserters 200 and prepared for stereotactic insertion, step 504. As shown in FIG. 3, the loop 108 at the distal portion 102 of the microcatheter 100 is placed around the distal portion 204 of the stylet 202. The length of the microcatheter 100 rests apposed to the inserter 200 tubing, temporarily being held together with the loop 108 distally and proximally by bone wax or other suitable material to fix the microcatheter 100 to the guide tube 200. This step may include prefilling the microcatheters 100 with therapeutic and attaching them to a filled syringe 302. Alternatively, the filled microcatheter may be capped until attached to the syringe 302. The system may be prepared in advance and purged of air, if necessary.

At step 506, one or more burr hole(s) are drilled, the dura is incised, and each microcatheter 100 is advanced, in turn, to the predetermined target area 306 as directed by the inserter 200. A single burr hole may accommodate multiple microcatheters 100, or two or more burr holes may be created based on the configuration of microcatheters 100 required to reach the desired targets.

The inserter 200 with the microcatheter 100 coupled, via the loop 108, to the distal portion 204 of the stylet 202 is directed, or "pushed through" to the target location or region. The rigidity of the inserter 200 and the stylet 202 combine to "pull" the microcatheter 100 along as the microcatheter itself is too flexible to be "pushed" through the body, e.g., through brain matter.

At step 508, the stylet 202 is withdrawn through the inserter 200 to release the loop 108. As above, the thumbscrew 210 is unscrewed, allowing the stylet 202 to be withdrawn proximally from within the stainless steel guide tube 200 thus releasing the microcatheter loop 108 and allowing the microcatheter 100 to be positioned at the desired location independently.

Once a microcatheter 100 is in the desired location, the inserter 200 is withdrawn and the microcatheter 100 is anchored to the rim of the burr hole using, for example, a small amount of adhesive, step 510. The adhesive produces a "spot weld" which will hold the microcatheter 100 in place but release the microcatheter 100 when sufficient force in a direction opposite of insertion is applied at the time of microcatheter 100 removal. A fast-curing, FDA-approved, silicon adhesive, or the like, may be used.

Alternatively, the surgeon can, after all the desired microcatheters 100 are positioned, fill the burr hole, with an array of microcatheters 100 emerging therefrom, with fibrin glue such as Tisseal, or the like.

The scalp is then closed around the microcatheters 100 using standard procedures. The microcatheters 100 may be looped atop the patient's head, to allow freedom of movement or "slack" in the event that the microcatheters 100 are inadvertently pulled. The syringes 302 attached to each microcatheter 100 are mounted into the infusion pump 304.

Alternatively, or in addition, the microcatheters 100 can be provided together, i.e., as a bundle, and threaded through larger-diameter flexible tubing (not shown) to provide protection to individual microcatheters 100.

Figure 4:
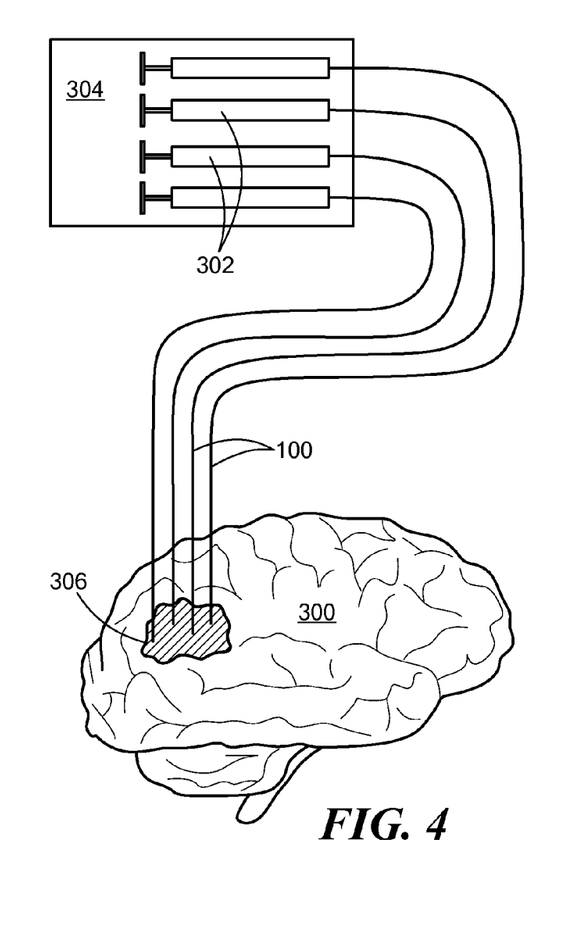
FIG. 4 is a schematic diagram showing the configuration of an array of microcatheters placed within a tumor in the brain in accordance with one embodiment of the present invention.

The therapeutic is then delivered at the appropriate rate, or sequence of rates, using the infusion pump 304, for the duration of the infusion protocol (minutes to days), step 512. After insertion of a microcatheter 100 at a desired location in, for example, a brain 300, as shown in FIG. 4, the proximal end 106 is attached to a therapeutic-filled syringe 302 connected to an infusion pump 304. An infusion pump 304, as known to those of ordinary skill in the art, may be used to control the rate of infusion of the therapeutic. As shown in FIG. 4, multiple microcatheters 100 may be inserted, each of which is connected to a respective single syringe 302. In an alternative embodiment, two or more microcatheters 100 may be connected to the same syringe 302. In yet another embodiment, a single microcatheter 100 may be connected to multiple syringes 302, for example, in order to deliver alternate therapeutics or therapeutics that are combined at delivery.

Upon completion of the infusion protocol, the microcatheters 100 are removed by applying a pulling force in the direction opposite to that of microcatheter 100 entry so as to overcome the adhesive anchor at the rim of the burr hole, step 514. The anchor is the only point of fixation and is designed to release the microcatheters 100. The microcatheters 100 can be removed by pulling until their entire length is withdrawn from the brain, exiting through the burr hole and the closed scalp incision.

The removal of the microcatheters 100 does not necessarily require reopening the scalp incision. The decision of whether or not to open the incision, however, is up to the physician and based on the circumstances of the case.

The systems and methods described herein are suitable for short-term, long-term, or permanent ongoing delivery of therapeutic within the brain or spinal cord including malignant or non-malignant brain tumors. The malignant brain tumor may be one of: a tumor of the neural cells, a tumor of the glial cells, or a tumor of both neural and glial cells.

Other applications may include infusion of growth factors, angiogenesis factors, antioxidants, vectors to deliver genes, or any fluid material to be infused within the CNS or elsewhere in the body.

Similarly, these systems and methods can be adapted for delivery of therapeutic to virtually any other area of the body, such as internal organs, e.g., liver, pancreas, spleen, kidney, heart, and skin. Still further, tissue can be treated including, but not limited to, normal tissue, ischemic tissue, cystic tissue, neurodegenerating tissue, or otherwise diseased or dysfunctional tissue.

Infusion of therapeutics using these systems and methods may employ other pumping devices as alternatives to the infusion pump described. Pumping devices may be positioned outside of the body or they may be implanted within the body, such as subcutaneously or within a cavity, e.g., intraperitoneally. Pumping devices may be automated, may operate through an osmotic mechanism, e.g., mini-osmotic pump, or may be controlled by the health care provider or the patient herself.

The microcatheter 100 may come loose from the guide tube 200 and stylet 204 during insertion. It may be possible for the physician or operator to detect that the microcatheter 100 is no longer progressing toward the target area due to a loss of tension on the microcatheter 100. In a situation where the tension, or loss thereof, cannot be detected by feel, however, inaccurate placement of the microcatheter 100 may result.

Figure 6:
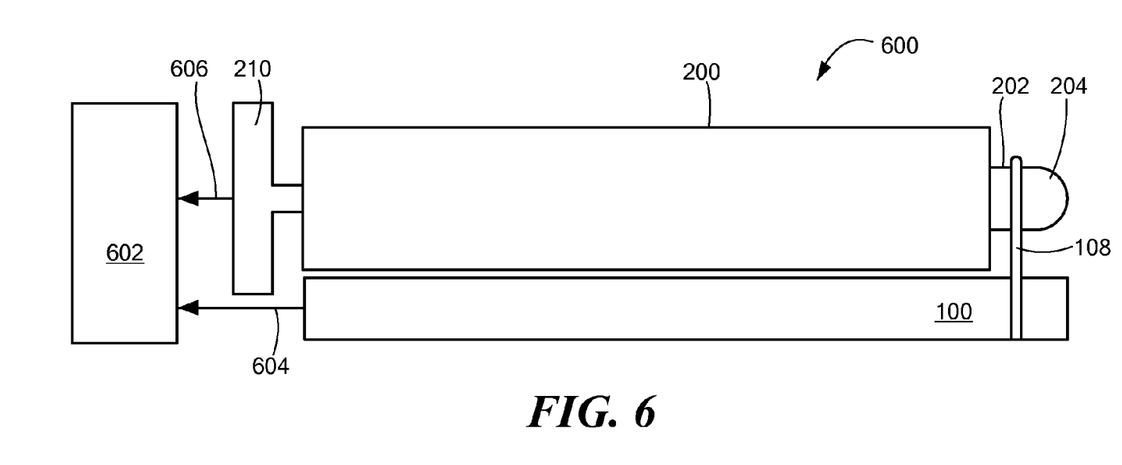
FIG. 6 is an alternate system in accordance with one embodiment of the present invention.

Referring now to FIG. 6, in accordance with one embodiment of the present invention, a system 600 is provided where the tension on the microcatheter 100 is monitored as it is being placed in position. A strain gauge 602 is coupled, via a connector 604, to the microcatheter 100 and to the stylet 202 via a connector 606. The strain gauge 602 measures the tension on each of the stylet 202 and the microcatheter 100. The strain gauge 602 can be set to issue an alarm if there is a relative change between the two measurements. Alternatively, the strain gauge may be connected to only the microcatheter 100 and when there is either a loss of tension detected, or the level of tension falls below a predefined threshold, an alarm indicating that, perhaps, the microcatheter 100 has uncoupled from the stylet 202, would sound.

Figure 7:
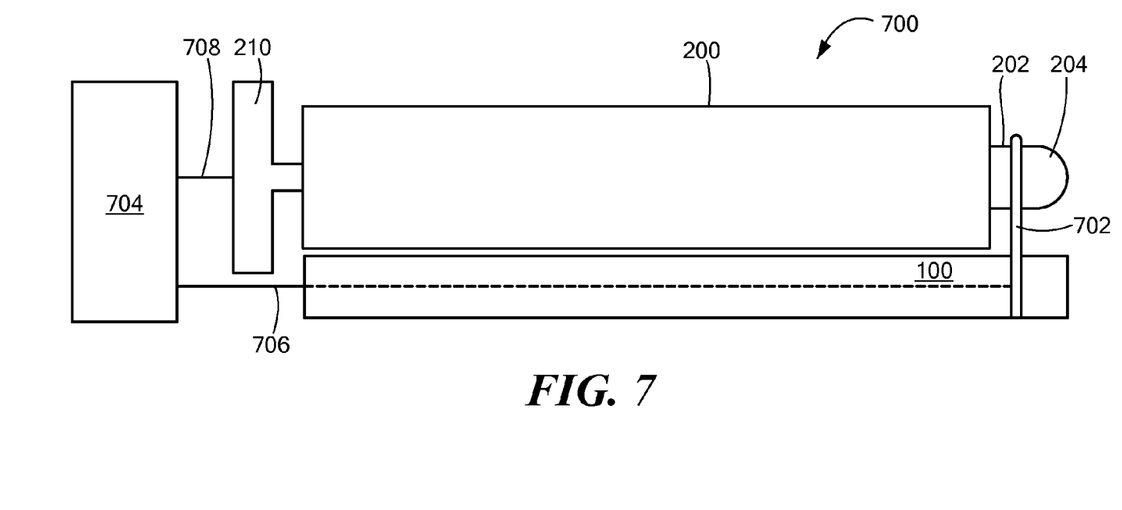
FIG. 7 is an alternate system in accordance with another embodiment of the present invention.

Referring now to FIG. 7, a system 700 provides an alternate embodiment, according to one aspect of the present invention, for determining that the microcatheter 100 has disconnected from the stylet 202. In this embodiment, a loop 702 is made from stainless steel or a similar conductive material and couples the microcatheter 100 to the stylet 202. A continuity tester 704 is coupled, via a very thin wire 706 to the loop 702. In addition, the continuity tester 704 is coupled, via a second wire 708 to the thumbscrew 210 and, therefore, completes a circuit through the stylet 202, the loop 702, and the wire 706. If the loop 702 disconnects from the stylet 202, the circuit will be broken and an indication of such, for example, an alarm, will notify the operator or physician. The wire 706 may run down through the microcatheter 100 and be connected to the loop 702 or the wire 706 may run along the outside of the microcatheter 100 and connect to the loop 702.

Figure 8:
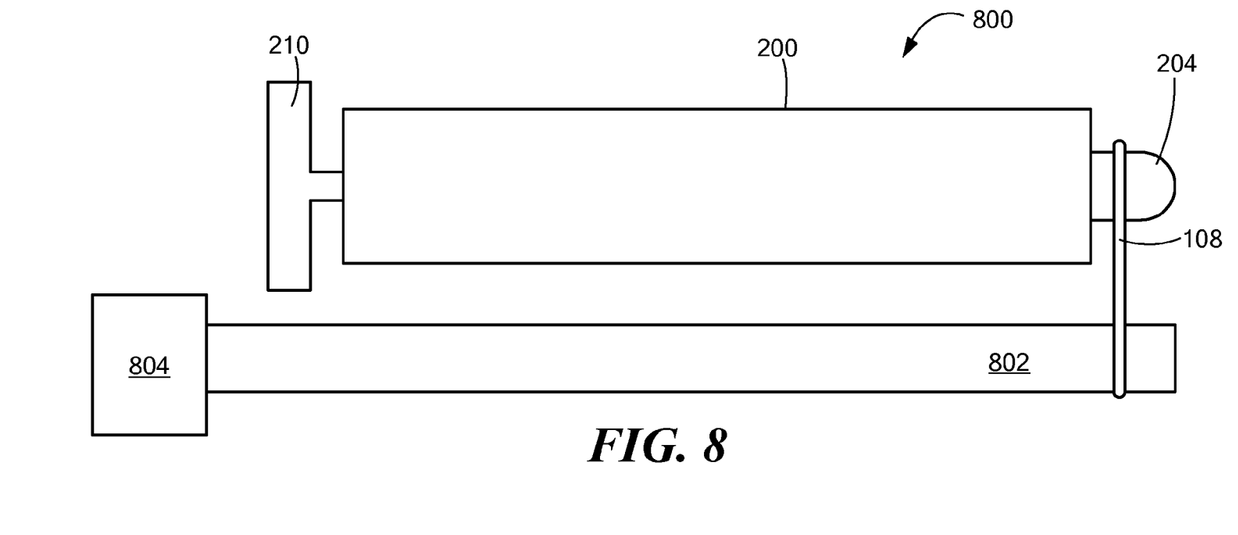
FIG. 8 is an alternate system where a fiber optic waveguide is provided in accordance with one embodiment of the present invention.

In one embodiment, referring now to FIG. 8, in a system 800 the microcatheter 100 is replaced by an optical waveguide 802, e.g., fiber optic material. Similar to that shown in FIGS. 2A and 3, the waveguide 802 is coupled to the guide tube 200 by the loop 108 for insertion at the desired location. A proximal end of the waveguide 802 is coupled to a light energy source and/or camera device 804. The device 804 may either provide light energy through the waveguide or capture images. The light energy may be IR, UV or any other frequency necessary to provide, for example, photodynamic therapy or the like. The choice of material for the optical waveguide 802 is understood by one of ordinary skill in the art and will depend on, among other parameters, the frequency of the light energy to be delivered, the power of the device 804 and the distance over which the light energy is directed.

Thus, where a plurality of microcatheters 100 are inserted, one could be an optical waveguide in order to facilitate photodynamic therapy at the desired location. Photodynamic therapy is performed by injecting a photoreactive agent into a tumor site, via one or more of the microcatheters 100, and then transmitting light through the optical waveguide to irradiate the photoreactive agent.

Figure 9:
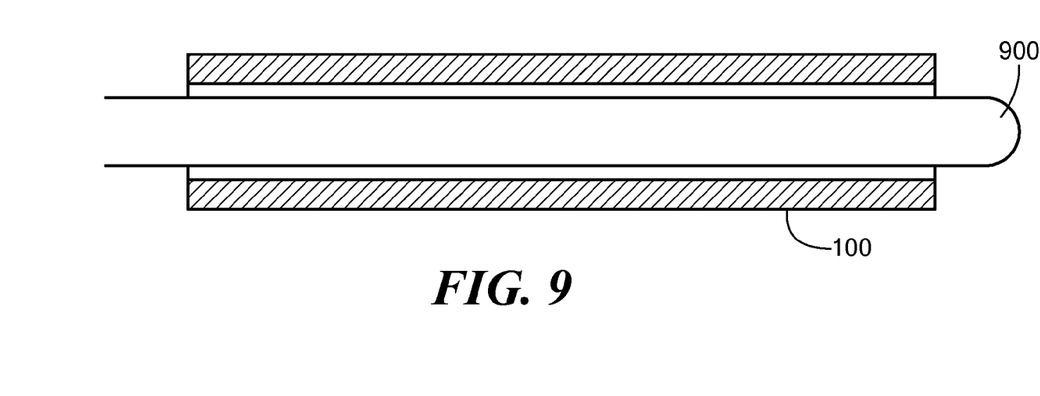
FIG. 9 is an alternate system in accordance with another embodiment of the present invention.

In an alternate embodiment, shown in FIG. 9, the microcatheter 100 contains a rigid guide 900, thus allowing the microcatheter 100 to be placed at any depth within the brain without the need for being "piggy-backed" on the inserter. The rigid guide 900 may be a stylet, as described above, in order to provide the microcatheter 100 with sufficient rigidity during insertion.

In operation, the microcatheter 100, with the rigid guide 900 within, is directed to the target location in, for example, the brain. As above, a number of microcatheters 100 may be provided where each is directed to a different location in order to provide therapeutic to the desired targets. Once the microcatheter 100 is fixed into position, the guide is removed from within. Similar to the process described above, a therapeutic is delivered through the lumen of the microcatheter 100 by connection to, for example, a syringe 302.

The microcatheter 100 of the embodiments of the present invention provide therapeutic via convection enhanced delivery with minimum backflow. Further, the patient is more comfortable due to the flexibility of the catheter and its ease of positioning. Multiple microcatheters can be positioned to provide full coverage of the therapeutic to one or more targeted regions. The microcatheter 100 is guided to, and positioned at, the desired location by operation of being either "piggy-backed" on the guide tube or by operation of a guide releasably placed in the microcatheter lumen.

It is appreciated that certain features of the invention, which are, for the sake of clarity, described in the context of separate embodiments, may also be provided in combination in a single embodiment. Conversely, various features of the invention, which are, for brevity, described in the context of a single embodiment, may also be provided separately or in any suitable subcombination.

Although various exemplary embodiments of the present invention have been disclosed, it will be apparent to those skilled in the art that changes and modifications can be made which will achieve some of the advantages of the invention without departing from the spirit and scope of the invention. It will be apparent to those reasonably skilled in the art that other components performing the same functions may be suitably substituted.

What is claimed is:

1. An apparatus for delivering a therapeutic to a location in a body, the apparatus comprising:
    a hollow guide tube comprising a single lumen therethrough with distal and proximal openings, the guide tube comprising an outer diameter in a range of 0.5 to 1.2 mm;
    a stylet, having proximal and distal portions, disposed within the guide tube lumen, wherein the stylet distal portion extends distally from the guide tube distal opening;
    a catheter having a catheter lumen running from a distal opening to a proximal opening, the catheter lumen having a diameter in a range of 0.03 to 2.11 mm; and
    a fixed diameter loop fixedly attached only to an exterior of the catheter at a catheter distal portion, the loop releasably coupled to the stylet distal portion.

2. The apparatus of claim 1, wherein the loop comprises at least one of:
    suture material; stainless steel; and a biologically inert material.

3. The apparatus of claim 1, wherein the loop is one of:
    welded to the exterior of the catheter; wrapped around the exterior of the catheter; integral with the exterior of the catheter; and glued to the exterior of the catheter.

4. The apparatus of claim 1, wherein:
    the guide tube comprises a threaded portion; and
    the stylet comprises a threaded portion,
    wherein the tube threaded portion is coupled to the stylet threaded portion.

5. The apparatus of claim 1, wherein the stylet comprises at least one of:
    stainless steel, platinum, cobalt, titanium, tantalum, and any alloy thereof.

6. The apparatus of claim 1, wherein the catheter comprises:
    optical waveguide material to carry light energy from the proximal opening to the distal opening.

7. The apparatus of claim 1, wherein:
    the guide tube comprises a first amount of flexibility; and
    the catheter comprises a second amount of flexibility,
    wherein the catheter is significantly more flexible than the guide tube.

8. The apparatus of claim 1, further comprising:
    a strain gauge, coupled to the catheter, to measure force exerted on the catheter during an insertion procedure.

9. The apparatus of claim 8, wherein:
    the strain gauge is coupled to the guide tube to measure force exerted on the guide tube during the insertion procedure.

10. The apparatus of claim 9, wherein:
    the strain gauge is configured to measure a difference between the force exerted on the catheter and the force exerted on the guide tube.

11. The apparatus of claim 1, wherein the stylet and the catheter are electrically coupled to one another to create a circuit, the apparatus further comprising:
    a device configured to detect when the circuit is opened.

12. The apparatus of claim 1, further comprising:
    a therapeutic within the catheter lumen.

13. The apparatus of claim 12, wherein the therapeutic comprises at least one of:
    a gel; a liquid; a solid; a gas; a capsule; and a powder.

14. A convection enhanced delivery system kit for delivering a therapeutic to a location in a body, the kit comprising:
    a hollow guide tube comprising a single lumen therethrough with distal and proximal openings, wherein the guide tube has an outer diameter in a range of 0.5 mm to 1.2 mm;
    a stylet, having proximal and distal portions, configured to be disposed within the guide tube lumen, wherein the stylet distal portion is configured to extend distally from the guide tube distal opening;
    a catheter having a catheter lumen running from a distal opening to a proximal opening, the catheter lumen having a diameter in a range of 0.03 mm to 2.11 mm;
    a fixed diameter loop fixedly attached only to an exterior of the catheter at a distal portion of the catheter and configured to be releasably coupled to the stylet distal portion; and
    printed instructions for informing a user how to assemble and use the hollow guide tube, stylet, and catheter to deliver a therapeutic by convection enhanced delivery.

15. The kit of claim 14, wherein the loop comprises at least one of:
    suture material; stainless steel; and a biologically inert material.

16. The kit of claim 14, wherein the loop is one of: welded to the exterior of the catheter; wrapped around the exterior of the catheter; integral with the exterior of the catheter; and glued to the exterior of the catheter.

17. The kit of claim 14, wherein:
    the guide tube comprises a threaded portion; and
    the stylet comprises a threaded portion,
    wherein the tube threaded portion is configured to be coupled to the stylet threaded portion.

18. The kit of claim 14, wherein the stylet comprises at least one of:
    stainless steel, platinum, cobalt, titanium, tantalum, and any alloy thereof.

19. The kit of claim 14, wherein:
    the guide tube comprises a first amount of flexibility; and
    the catheter comprises a second amount of flexibility,
    wherein the catheter is significantly more flexible than the guide tube.

20. The kit of claim 14, further comprising:
    a strain gauge configured to be coupled to the catheter to measure force exerted on the catheter during an insertion procedure.

21. The kit of claim 20, wherein:
    the strain gauge is further configured to be coupled to the guide tube to measure force exerted on the guide tube during the insertion procedure.

22. The kit of claim 21, wherein:
    the strain gauge is further configured to measure a difference between the force exerted on the catheter and the force exerted on the guide tube.

23. The kit of claim 14, wherein:
    the stylet and the catheter are configured to be electrically coupled to one another to create a circuit, the kit further comprising:
    a device configured to detect when the circuit is opened.

* * * * *